(12) United States Patent
Kumar et al.

(10) Patent No.: US 6,393,763 B1
(45) Date of Patent: May 28, 2002

(54) METHOD FOR MAXIMIZATION OF ARTEMISININ PRODUCTION BY THE PLANT ARTEMISIA ANNUA

(75) Inventors: Sushil Kumar; Shiv Kumar Gupta; Madan Mohan Gupta; Ram Kishor Verma; Dharam Chand Jain; Ajit Kumar Shasany; Mahendra Pandurang Darokar; Suman Preet Singh Khanuja, all of Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/538,892

(22) Filed: Mar. 30, 2000

(51) Int. Cl.$^7$ .............................................. A01B 79/00
(52) U.S. Cl. ....................................................... 47/58.1
(58) Field of Search ........................................... 47/58.1

(56) References Cited

PUBLICATIONS

J.C. Laughlin Effect of Agronomic practices on plant yield and anti–malarial constituents of Artemisia annua L. Acta Horticulturae 331, 1993.*
J.C. Laughlin The influence of distribution of antimalarial constituents in Artemisia annu I. on time and method of harvest. Acta Horticulturae 390 Nov. 1995.*
N. Delabays et al. The evolution of the artemisinin content in Artemisia Annua L. during one growing season. Atti convegno internazionale: Coltivazione e miglioramento di piante officinali, Trento, Italy, 2–3 guigno 1994, (1996) pp 635–638 4 ref.*
Muni Ram et al. Effect of planting Time on the Yield of Essential Oil and Artemisinin in Artemisia annua under Subtropical conditions. J. Essent. Oil Res., 9, 193–197 (Mar/Apr 1997).*

* cited by examiner

Primary Examiner—Bruce R. Campbell
Assistant Examiner—A Para
(74) Attorney, Agent, or Firm—Merchant & Gould P.C.

(57) ABSTRACT

The invention provides a method for maximization of artemisinin yield of the plant Artemisia annua, said method comprising sowing seeds of Artemisia annua plant on raised bed nursery during second and third week of December and maintaining the moisture throughout; transplanting seedlings thus obtained bearing at least 5–15 leaves into the main field fertilized with fertilizer, preferably NPK @ 80,40,40 kg/ha to achieve a population density of 50,000 to 200,000 per ha followed by light irrigation in the second week of March and irrigation every fortnight thereafter; harvesting the crop four times by cutting the plant tops leaving 75–100 cm part of plant for further regeneration, the said harvests are performed in a manner that the first harvest is done in fourth week of May, second harvest in third week of July, third harvest in second week of September and fourth harvest in third week of October of each year; and at each harvesting time care is taken to care at least one green branch, and extracting artemisinin from the plant tissue immediately after each harvest.

8 Claims, 1 Drawing Sheet

METHOD FOR MAXIMIZATION OF ARTEMISININ PRODUCTION BY THE PLANT ARTEMISIA ANNUA

FIELD OF INVENTION

This invention relates to a method for maximization of artemisinin production by the plant *Artemisia annua* belonging to family: Asteraceae. More particularly, the invention is developed through agro-technology involving method of optimizing the planting time, transplanting scheduling, population density, number of harvests and harvesting schedule leading to enhanced yields of artemisinin and related metabolites which have pharmaceutical value of anti-infectives, particularly as antimalarial drug.

BACKGROUND OF INVENTION

The plant *Artemisia annua* (family: Asteraceae) is valued for producing a sesquiterpenoid lactone endoperoxide named 'artemisinin' which is a promising antimalarial drug and effective against *Plasmodium falciparum, P. vivax* and drug resistant parasites at nanomolar concentration. The compounds α and β arteethers which are synthesized from dihydroartemisinin by etherification with ethanol, were developed as antimalarial drug in India by Central Institute of Medicinal and Aromatic Plants (CIMAP), Lucknow and Central Drug Research Institute (CDRI), Lucknow after phase III clinical trial. Artemisinins are active against *Schistosoma mansoni* and *S. japonicum*, in-vitro and in experimental animal models. These compounds are also active against *Leishmania major, Toxoplasma gondii* and *Pneumocystis carinii* in-vitro and against *P.carinii* in-vivo. Artemisinins have immunosuppressive activity and also potential anticancer activity. Considering the importance of artemisinins which is tedious and difficult to synthesize chemically an all out programme was undertaken to develop *Artemisia annua* plant varieties with high artemisinin content, development of agrotechnology for increase yield of these compounds, followed by improved extraction procedure. In this direction the inventors were successful in developing and releasing a variety named "Jeevan Raksha" from an isolated population containing high artemisinin in the foliage (0.5 to 1.0%) (Sushil Kumar et al. 1999. Journal of Medicinal and Aromatic Plant Sciences. 21:47–48.) This plant "Jeevan Raksha" not only produces high artemisinin but also maintains the synchronized conversion to higher level of artemisinin during May to October. As the content of artemisinin fluctuates from zero level at the time of planting to more than 0.4 to 1.00% during May and June with subsequent functions of increase till October, it was necessary to scientifically develop cultivation methodology for the crop to maximize the vigour of the foliage and biosynthesis of artemisinin by systematic scheduling. For this purpose the inventors carried out planned experiments with variation in planting times, population density and number of harvest from the crop to increase the yield from limited area within optimum span of time.

OBJECT OF THE INVENTION

The main object of the invention relates to a method for maximize the artemisinin yield of the plant *Artemisia annua* by scheduling transplanting time and following a multiple harvesting schedule coinciding with the higher artemisinin accumulation in the plant.

In another object of the invention relates to provide a method for maximizing the yield of artemisinin to the tune of 85–95 kg/ha by following the schedule of the invention.

In yet another object of the invention relates to a method wherein the yield of artemisinin is maximized by maintaining the schedule defined in the invention for different transplanting time of the plant.

SUMMARY OF THE INVENTION

To meet the above objects and others, the present invention provides a method for maximizing the artemisinin yield of the plant *Artemisia annua* by scheduling transplanting time and following a multiple harvesting schedule coinciding with the higher artemisinin accumulation in the plant, wherein the method comprises of the following steps;

(a) sowing seeds of *Artemisia annua* plant on raised bed nursery during second and third week of December and maintaining the optimum moisture throughout, (b) transplanting seedlings thus obtained bearing at least 5–15 leaves into the main field fertilized with NPK @ 80,40,40 kg/ha to achieve a population density of 50,000 to 2,00,000 per ha followed by light irrigation in the second week of March and irrigation every fortnight there after, c) harvesting the crop four times by cutting the plant tops leaving 75–100 cm part of plant for further regeneration, the said harvests are performed in a manner that the first harvest is done in fourth week of May, second harvest in third week of July, third harvest in second week of September and fourth harvest in third week of October of each year, and at each harvesting time care is taken to care at least one green branch, and d) extracting artemisinin from the plant tissue immediately after each harvest.

DETAILED DESCRIPTION

It is therefore a intent of the invention to provide the crop of *Artemisia annua*, a process for increasing the foliage harvest coupled with the maximum artemisinin yield.

The phenotype of a plant is the consequence of interaction between the genotype and the environment. The genotype is the genetic make up which directs the plant to express all characters. But proper expression needs the signal from the environment to express at a particular time, stage and tissue. This is called temporal and spatial expression of genetic traits, which includes synthesis of important chemicals and secondary metabolites like artimisinin in case of *Artemisia annua*. Based on this fact, it is correct to predict that a plant is not likely to produce and accumulate secondary metabolite just after germination from the seed. Same is true in case of the plant *Artemisia annua* requiring a certain stage of maturity to start producing artemisinin. Now at the time of production of the compound artemisinin, the plant should have sufficient foliage to accumulate this secondary metabolite. Further, the fluctuating environmental conditions also fluctuate the synthesis of these products. A better genotype responds to these signals in a more vigorous way compared to a weak genotype. At the macro level of commercial crop cultivation in the field environment cannot be manipulated as in the case of cultures in the laboratory. However, critical factors like planting date, number of harvests, harvesting schedules and population density can be manipulated for adjusting to the environmental conditions for maximizing the crop as well as critical chemical production.

With these objective, planned experiments were carried out on the high yielding plant variety "Jeevan Raksha" of *Artemisia annua*, to optimize the agrotechnological process to maximize the yield of herbage and thus artemisinin in a single season so that the method, sequence and optimized scheduling approach can be utilized universally with varying crop seasons in different climatic regions globally by skilled modifications.

Figure 1:
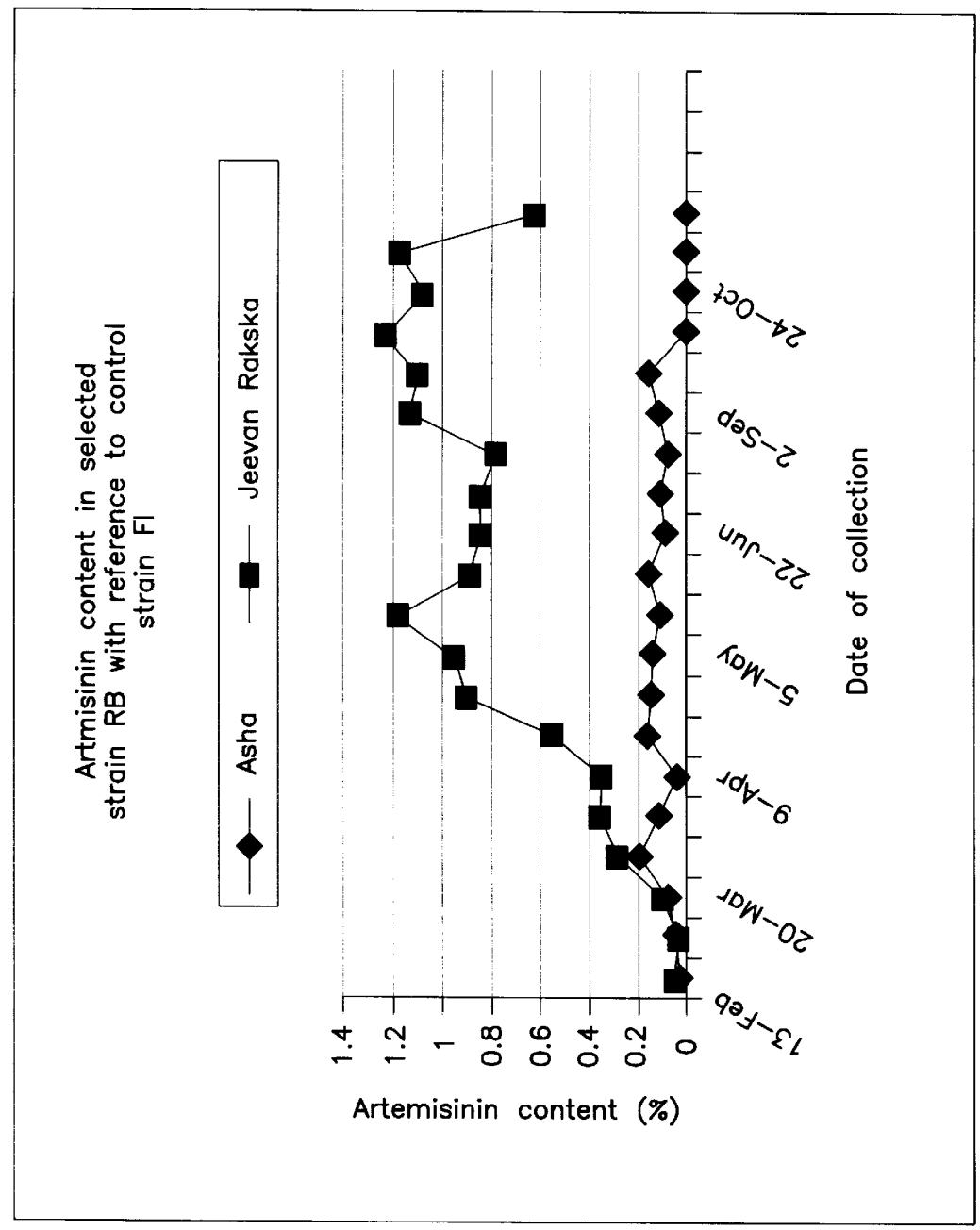
FIG. 1 is a graph showing Artemisinin content in selected strain (RB) with reference to control strain (F1)

The following examples explain in details the planned experiments and the analysis carried out for maximizing yields with the consistent results thus obtained over three years of field evaluation.

EXAMPLE 1

Effects of variation in the date of transplantation of crops and number of harvests taken there from, on the expression of plant growth and artemisinin yield related traits in *Artemisia annua*

The seeds of "Jeevan Raksha" were shown on raised bed nurseries for the plant in the month of December ($14^{th}$ December) and the seedlings obtained were transplanted to the plots of 5×5 $m^2$ size arranged in a randomized block design. The planting dates were second week of February, fourth week of February, second week of March, fourth week of March, and second week of April. For each planting date, 4 replicated treatments for single, double, triple and fourth harvests were designed and the foliage was harvested as planned, after specified days transplantation (Table 1). In particular the harvesting dates were coincided as follows:
One harvest: Third week of October
Two harvests: First in fourth week of May, second in third week of October.
Three harvests: First in fourth week of May, second in third week of July and third in third week of October.
Four harvests: First in fourth week of May, second in third week of July and third in second week of September and fourth in third week of October.

The harvesting time after the date of transplanting mentioned in the table are not absolute figures and are given for understanding. These figures vary but if harvested in the same week then the yield remain consistent.

Date of Transplanting: Second Week of February

Only one harvest after 242 days yielded 222 q shoot mass per ha, 47 q leaf per ha, artemisinin 0.60% in leaves with total artemisinin of 27.2 kg/ha and artemisinin harvest index 0.14. The corresponding figures for two harvests combined after 101 and 242 days were 53 q/ha leaf yield, 0.55% artemisinin, 28.9 kg/ha artemisinin and 0.17 artemisinin harvest index. In 3 harvests after 101, 156 and 242 days the leaf yield (104 q/ha), artemisinin (0.65%) content, artemisinin yield (66.9 kg/ha) and artemisinin harvest index (0.20) increased considerably. When the crop was harvested 4 times continuously though the shoot mass yield, stem mass yield, leaf yield decreased marginally from the 3 combined harvests, the leaf harvest index, leaf yield/stem/ mass ratio and the average percentage of artemisinin in leaves increased which resulted in maximum yield of artemisinin per ha (69.4 kg/ ha) and highest artemisinin harvest index in this date of transplanting. So in this method, within the same crop duration, performing several harvests and allowing the plant to regenerate after each harvest the total harvest of artemisinin can be maximized in the field.

Date of Transplanting: Fourth Week of February

If the transplanting is delayed and crop is planted later, four harvesting definitely increases the artemisinin yield than the single harvest but the yield is less than the early planting on $14^{th}$ February (Table 1).

Date of Transplanting: Second Week of March

In this experiment highest leaf harvest index (0.41), artemisinin content (0.84%), artemisinin yield (91.6 kg/ha) and artemisinin harvest index 0.34 was obtained for the four harvests combine (77, 132, 186, 216 days after transplanting). The single harvest after 216 days, two harvests after 77 and 216 days or three harvests after 77, 132 and 216 days yielded less artemisinin compared to the four combine harvests.

Date of Transplanting: Fourth Week of March

Though the yield increased with increased number of harvests, still it was very less than the four harvests result of second week of March date of transplanting. In this date of transplanting four cutting from the same crop drastically reduced the yield of artemisinin as sufficient time for regeneration of foliage and differentiation to accumulate artimisinin was not available.

Date of Transplanting: Second Week of April

Similar type results were obtained as in case of $4^{th}$ week of March date of transplanting with reduced artemisinin yield (Table 1).

TABLE 1

Effects of variation in the date of transplantation of crops and number of harvests taken therefrom on the expression of plant growth and artemisinen yield related traits in *Artemisia annua*

| | | | | | | | | | | | |
|---|---|---|---|---|---|---|---|---|---|---|---|
| 1 | 14 Feb | 1 | 242 | $222^a$ | $175^a$ | $47^a$ | $0.22^{a,b}$ | $0.29^{a,b}$ | $0.60^a$ | $27.2^a$ | $0.14^{a,b,c}$ |
| 2 | 14 Feb | 2 | 101, 242 | $169^a$ | $115^a$ | $53^a$ | $0.32^{c,d}$ | $0.46^{b,c}$ | $0.55^a$ | $28.9^{a,b}$ | $0.17^{a,b,c}$ |
| 3 | 14 Feb | 3 | 101, 156, 242 | 353 | 249 | $104^b$ | $0.31^{b,c}$ | $0.45^{b,c}$ | $0.65^a$ | $66.9^c$ | $0.20^{b,c}$ |
| 4 | 14 Feb | 4 | 101, 156, 210, 242 | $302^a$ | $200^a$ | $102^b$ | $0.34^{c,d}$ | $0.53^c$ | $0.69^b$ | $69.4^c$ | $0.24^{c,d}$ |
| 5 | 27 Feb | 1 | 227 | $261^a$ | $225^a$ | $36^a$ | 0.14 | $0.16^a$ | $0.45^{a,b}$ | $16.3^a$ | $0.06^a$ |
| 6 | 27 Feb | 2 | 84, 227 | $245^a$ | $185^a$ | $60^{e,f}$ | 0.25 | $0.33^f$ | $0.58^{c,d}$ | $32.4^{c,d}$ | $0.13^d$ |
| 7 | 27 Feb | 3 | 84, 155, 227 | $250^a$ | $188^a$ | $62^{e,f}$ | 0.25 | $0.33^f$ | $0.64^{d,e}$ | $36.9^d$ | $0.15^d$ |
| 8 | 8 March | 1 | 216 | $209^a$ | $156^a$ | $53^a$ | $0.26^{a,b,c}$ | $0.35^{a,b,c}$ | $0.46^a$ | $21.0^a$ | $0.10^{a,b}$ |
| 9 | 8 March | 2 | 77, 216 | $237^a$ | $196^a$ | $40^a$ | $0.20^a$ | $0.26^a$ | $0.45^a$ | $18.1^a$ | $0.09^a$ |
| 10 | 8 March | 3 | 77, 132, 216 | $171^a$ | $114^a$ | $57^a$ | $0.34^{c,d}$ | $0.51^c$ | $0.59^a$ | $33.6^b$ | $0.20^{b,c}$ |
| 11 | 8 March | 4 | 77, 132, 186, 216 | $275^a$ | $161^a$ | $114^b$ | $0.41^d$ | 0.70 | $0.84^b$ | 91.6 | $0.34^d$ |
| 12 | 25 Mar | 1 | 206 | $254^a$ | $213^a$ | $41^{a,b}$ | 0.16 | $0.19^{a,b}$ | $0.39^a$ | $15.7^a$ | $0.06^a$ |
| 13 | 25 March | 2 | 89, 206 | $268^a$ | $221^a$ | $47^{a,b,c}$ | 0.17 | $0.21^a$ | $0.54^c$ | $22.1^{a,b}$ | $0.08^{a,b}$ |
| 14 | 25 March | 3 | 89, 145, 206 | 318 | 249 | $70^f$ | 0.22 | $0.28^{c,d,e,f}$ | $0.61^{c,d,e}$ | $38.0^d$ | $0.12^{c,d}$ |
| 15 | 25 March | 4 | | | | | | | | | |
| 16 | 29 Mar | 1 | 200 | $282^a$ | $229^a$ | $53^{b,c,d,e}$ | 0.19 | $0.23^{b,c}$ | $0.42^{a,b}$ | $22.3^{a,b}$ | $0.08^{a,b}$ |
| 17 | 29 March | 2 | 123, 200 | $278^a$ | $213^a$ | $65^{e,f}$ | 0.24 | $0.31^{e,f}$ | $0.67^e$ | 41.6 | $0.15^d$ |

TABLE 1-continued

Effects of variation in the date of transplantation of crops and number of harvests taken therefrom on the expression of plant growth and artemisinen yield related traits in *Artemisia annua*

| 18 | 29 March | 3 | 69, 123, 200 | 260$^a$ | 196$^a$ | 64$^{e,f}$ | 0.25 | 0.33$^f$ | 0.61$^{c,d,e}$ | 37.0$^d$ | 0.14$^d$ |
|---|---|---|---|---|---|---|---|---|---|---|---|
| 19 | 29 March | 4 | | | | | | | | | |
| 20 | 1 April | 1 | 193 | 201$^a$ | 170$^a$ | 30$^a$ | 0.16$^a$ | 0.19$^a$ | 0.50$^a$ | 15.1$^a$ | 0.08$^a$ |
| 21 | 1 April | 2 | 134, 193 | 196$^a$ | 159$^a$ | 36$^a$ | 0.18$^c$ | 0.23$^a$ | 0.54$^a$ | 19.6$^a$ | 0.10$^{a,b}$ |
| 22 | 1 April | 3 | | | | | | | | | |
| 23 | 1 April | 4 | | | | | | | | | |
| 24 | 13 April | 1 | 180 | 218$^{a,b}$ | 173$^{a,b}$ | 44$^{a,b}$ | 0.20$^a$ | 0.26$^a$ | 0.44$^{a,b}$ | 19.3$^a$ | 0.09$^b$ |
| 25 | 13 April | 2 | 127, 187 | 269$^a$ | 216$^a$ | 53$^{c,d,e}$ | 0.20 | 0.25$^{b,c,d,e}$ | 0.56$^{c,d}$ | 24.7$^{b,c}$ | 0.09$^{a,b,c}$ |
| 26 | 13 April | 3 | 70, 125, 187 | 257$^a$ | 197$^a$ | 60$^{d,e,f}$ | 0.23 | 0.30$^{d,e,f}$ | 0.62$^{c,d,e}$ | 33.2$^d$ | 0.13$^d$ |
| 27 | 22 June | 1 | 130 | 151$^a$ | 121$^a$ | 30$^a$ | 0.20$^a$ | 0.25$^a$ | 0.51$^b$ | 15.4$^a$ | 010$^b$ |
| | | | Sem | ±6 | ±5 | ±3 | ±0.01 | ±0.02 | ±0.03 | ±2.6 | ±0.01 |
| | | | CD, 5% | 45 | 40 | 9 | 0.03 | 0.04 | 0.06 | 6.0 | 0.02 |
| | | | CD, 10% | 61 | 53 | 12 | 0.04 | 0.06 | 0.08 | 8.1 | 0.03 |

The following conclusions were drawn from the experiments:

1. The most suitable date of transplanting to harvest the crop 4 times is second week of March followed by second week of February to get maximum yield of artemisinin.
2. The most suitable date of transplanting to harvest the crop 3 times is second week of February after which yield of artemisinin remain approximately constant up to second week of April.
3. Maximum artemisinin yield was obtained for two harvests on transplanting during fourth week of March followed by fourth week of February.
4. Maximum artemisinin yield was obtained for one harvests on transplanting approximately during second week of February followed by fourth week of of February.
5. Highest artemisinin in the foliage was obtained by following the schedule of 4 harvestings after transplanting on second week of March.
6. Harvesting the crop with a deviation of ±5 days did not affect the yield of artemisinin.
7. The yield remained fairly constant with a population of plant 50,000 to 2,000,000 per hectare.

EXAMPLE 2

Fluctuation of artemisinin content of the plant Jeevan Raksha in different month of the year.

The foliage samples were collected from the field in different months of the year, shade dried, extracted in hexane and concentrated under vacuum. Artemisinin was isolated by column chromatography on silica gel in the fractions of Hexane: Ethyl acetate (95:5) and Hexane: Ethyl acetate (90:10) and pure artemisinin was crystallized. For analysis, the fresh plant material (1g) was ground in 5 ml hexane in a mortar and pestle for 5 minute, filtered, evaporated and re-dissolved in 0.5ml hexane (for dried plant material: 0.2 g of dried plant material was extracted in 10 ml of hexane for 12 h repeatedly thrice, filtered, evaporated and re-dissolved in 0.5 ml hexane). The above extract (5 $\mu$l) and pure artemisinin solution (5 $\mu$l) were loaded on a TLC plate (60F$_{254}$, E, Merck, Germany). Chromatography was performed in glass tank saturated with hexane-diethylether (1:1) mobile phase. After about 8 cm mobility, the plate was dried, and the spots were visualized by immersing the plate in a freshly prepared mixture of glacial acetic acid: sulfuric acid: anisaldehyde (50:1:0.5), followed by heating the plate at 110° C. for 15 minutes to visualize the pink colour of artemisinin. For quantification, TLC spots corresponding to artemisinin was scanned at 540 nm using CAMAG TLC scanner. A calibration curve of pure artemisinin was used for quantification of artemisinin content pf the plant (Gupta et al. (1996) Journal of Medicinal and Aromatic Plant Sciences. 18: 5–6.).

As evident from FIG. 1, artemisinin synthesis in the plant continues to increase from the month of February and peaked during May with subsequent marginal decrease but maintained at a concentration from 0.8 to more than 1.0. From July to October again the artemisinin content increased to more than 1.0% with reduction in synthesis in the month of November. This trend of artemisinin synthesis was exploited to harvest the foliage at different time interval from the transplantation. Foliage from the variety "Jeevan Raksha" can be harvested till the month of November and dormancy is not observed like other varieties. But the harvesting scheduling can also be prepared by coinciding the harvesting time during maximum production of the active constituents.

Further, positive high correlations were obtained between artemisinin yield with leaf yield (0.97), % artemisinin in the leaves (0.92), number of harvests (0.82) (Table 2). So considering all these parameters the harvesting dates were coincided with the high % of artemisinin content of the leaves to increase the production of artemisin.

TABLE 2

Coefficient of correlation between the artemisinin yield related traits and number of harvests of crop in *Artemisia annua*

| Crop trait | Stem mass | Leaf yield | Leaf harvest index | Leaf/Stem ratio | % artemisinin in leaves | Artemisinin yield | Artemisinin harvest index | Number of harvests |
|---|---|---|---|---|---|---|---|---|
| Shoot mass | 0.87** | 0.59 | 0.15 | 0.15 | 0.37 | 0.51 | 0.25 | 0.37 |

TABLE 2-continued

Coefficient of correlation between the artemisinin yield related traits and number of harvests of crop in Artemisia annua

| Crop trait | Stem mass | Leaf yield | Leaf harvest index | Leaf/Stem ratio | % artemisinin in leaves | Artemisinin yield | Artemisinin harvest index | Number of harvests |
|---|---|---|---|---|---|---|---|---|
| Stem mass | | 0.14 | −0.33 | −0.34 | −0.04 | −0.06 | −0.23 | −0.02 |
| Leaf yield | | | 0.87** | 0.87** | 0.83** | 0.97** | 0.88** | 0.82** |
| Leaf harvest index | | | | 0.99** | 0.79** | 0.87** | 0.94** | 0.79** |
| Leaf/Stem ratio | | | | | 0.81** | 0.88** | 0.96** | 0.79** |
| % artimisinin in leaves | | | | | | 0.92** | 0.93** | 0.84** |
| Artimisinin yield | | | | | | | 0.95** | 0.82** |
| Artimisinin harvest index | | | | | | | | 0.83** | b = **, significant at 1% level.
a = Means of values obtained in two experiments The novelty of the invention is that the of scheduling of harvests with proper transplanting time, while cultivating *Artemisia annua* for artemisinin to increase the yield tremendously. So a process of crop scheduling was devised to maximize the artemisinin yield.

The process can be performed in the following steps to maximize the yield of artemisinin in a commercial plantation of *Artemisia annua*.

1. The seeds of the plant are sown on raised bed nursery during second and third week of December maintaining the moisture throughout.
2. The seedlings thus obtained bearing at least 5–15 leaves are transplanted to the main field (fertilized with NPK @ 80,40,40 kg/ha) to achieve a population density of 50,000 to 2,00,000 per ha followed by light irrigation in the second week of March and irrigation every fortnight there after.
3. Then the crop is harvested four times by cutting the top leaving 75–100 cm part of plant for further regeneration. The harvests are first in fourth week of May, second in third week of July and third in second week of September and fourth in third week of October. At the harvesting time care is taken that at least one green branch is also left.
4. After each harvest artemisinin from the plant tissue is immediately extracted out.
5. Following this schedule, the yield of artemisinin can be maximized to the tune of 80–95 kg/ha.
6. The schedule should be maintained for different transplanting time to maximize yield.

The very novel idea of harvesting scheduling can be applied to any crop of *Artemisia annua*, provided the study of artemisinin accumulation at different period of time is worked out based on which the crop can be harvested to extract artemisinin. The months mentioned in the description can also be varied with little skillful thought on the climatic conditions prevailing at a particular place and cropping season of *Artemisia annua*. But the basic process of relating the artemisinin content in the foliage and subsequent coinciding the harvesting time for the high yielding variety Jeevan Raksha for a bumper reaping of artemisinin is new to the crop and has utility in yield improvement.

What is claimed is:

1. A method to maximize the artemisinin yield of the plant *Artemisia annua* by scheduling transplanting time and following a multiple harvesting schedule coinciding with higher artemisinin accumulation in the plant, wherein the method comprises the following steps:
   (a) sowing seeds of *Artemisia annua* plant on a raised bed nursery during the second and third week of December and maintaining the moisture of said raised bed nursery;
   (b) transplanting seedlings thus obtained bearing at least 5 leaves into a main field fertilized with nitrogen/phosphorus/potassium fertilizer, at a concentration of about 80,40,40 kg/ha to achieve a population density of about 50,000 to 200,000 per ha followed by light irrigation in the second week of March and irrigation every fortnight thereafter,
   (c) harvesting the crop four times by cutting te plant tops, leaving about 75–100 cm of said plant for further regeneration, said harvests are performed in a manner that the first harvest is done in the fourth week of May, second harvest in the third week of July, third harvest in the second week of September and fourth harvest in the third week of October of each year, and at each harvesting care is taken to leave at least one green branch on the plant; and
   (d) extracting artemisinin from the plant tissue immediately after each harvest.

2. A method as claimed in claim 1 wherein the yield of artemisinin is maximized to about 85–95 kg/ha.

3. A method as claimed in claim 1 wherein the moisture content is maintained at the optimum level.

4. The method of claim 1, wherein seedlings bearing at least 15 leaves are transplanted.

5. The method of claim 1, wherein seedlings bearing 5–15 leaves are transplanted.

6. A method to maximize the artemisinin yield of the plant *Artemisia annua* by scheduling transplanting time and following a multiple harvesting schedule coinciding with higher artemisinin accumulation in the plant, wherein the method comprises the following steps:
   (a) sowing seeds of *Artemisia annua* plant on a raised bed nursery during the second and third week of December and maintaining the moisture of said raised bed nursery;
   (b) transplanting seedlings thus obtained bearing at least 5 leaves into a main field fertilized with nitrogen/phosphorus/potassium fertilizer, at a concentration of about 80,40,40 kg/ha to achieve a population density of about 50,000 to 200,000 per ha followed by light irrigation in the second week of February and irrigation every fortnight thereafter,
   (c) harvesting the crop four times by cutting the plant tops, leaving about 75–100 cm of said plant for further regeneration, said harvests are performed in a manner that the first harvest is done in the fourth week of May, second harvest in the third week of July, third harvest in the second week of September and fourth harvest in the third week of October of each year, and at each harvesting care is taken to leave at least one green branch on the plant; and (d) extracting artemisinin from the plant tissue immediately after each harvest.

7. A method to maximize the artemisinin yield of the plant *Artemisia annua* by scheduling transplanting time and following a multiple harvesting schedule coinciding with higher artemisinin accumulation in the plant, wherein the method comprises the following steps:

(a) sowing seeds of *Artemisia annua* plant on a raised bed nursery during the second and third week of December and maintaining the moisture of said raised bed nursery;

(b) transplanting seedlings thus obtained bearing at least 5 leaves into a main field fertilized with nitrogen/phosphorus/potassium fertilizer, at a concentration of about 80,40,40 kg/ha to achieve a population density of about 50,000 to 200,000 per ha followed by light irrigation in the second week of February and irrigation every fortnight thereafter, (c) harvesting the crop four times, by cutting the plant tops, leaving about 75–100 cm of said plant for further regeneration, and ensuring that at least one green branch is left on the plant; and (d) extracting artemisinin from the plant tissue immediately after each harvest.

8. The method of claim 7, wherein the first harvest is performed within 5 days before or after the fourth week of May, the second harvest is performed within 5 days before or after the third week of July, the third harvest is performed within 5 days before or after the second week of September, and the fourth harvest is performed with 5 days before or after the third week of October.

* * * * *